(12) United States Patent  
Alouani et al.

(10) Patent No.: US 8,860,579 B1  
(45) Date of Patent: Oct. 14, 2014

(54) ILLEGAL DRUG DETECTOR AND METHOD OF ITS USE

(76) Inventors: Ali T. Alouani, Cookeville, TN (US); Timothy R. Cook, Cookeville, TN (US)

( * ) Notice: Subject to any disclaimer, the term of this patent is extended or adjusted under 35 U.S.C. 154(b) by 380 days.

(21) Appl. No.: 13/412,726

(22) Filed: Mar. 6, 2012

(51) Int. Cl.  
*G08B 17/10* (2006.01)

(52) U.S. Cl.  
USPC .......................................................... 340/632

(58) Field of Classification Search  
CPC ..... B01L 3/5023; H04W 24/00; G08B 21/00; F24F 2011/0026; F24F 2003/1657; G01N 1/00; G01N 1/22  
USPC ............ 340/632, 506, 539.1, 618, 629, 13.24  
See application file for complete search history.

(56) References Cited

U.S. PATENT DOCUMENTS

| 6,602,702 | B1 * | 8/2003 | McDevitt et al. | 435/288.7 |
| 2008/0262321 | A1 * | 10/2008 | Erad et al. | 600/301 |
| 2009/0010808 | A1 * | 1/2009 | Kraft | 422/83 |
| 2012/0079871 | A1 * | 4/2012 | Williamson | 73/28.01 |
| 2012/0154578 | A1 * | 6/2012 | Bzorgi | 348/143 |

* cited by examiner

*Primary Examiner* — Phung Nguyen  
(74) *Attorney, Agent, or Firm* — Stephen J. Stark; Miller & Martin PLLC

(57) ABSTRACT

An illegal drug sensing device provides a sensor coupled to a processor which evaluates the likely presence of illegal drug consumption and/or manufacture at a particular location. Upon the processor determining that such a condition is likely, an alarm is transmitted to at least one of locally or remotely such as through wired or wireless systems which are employed to alert at least one interested party such as the authorities (i.e., the police department) or a land owner of the likely presence of illegal drug activity at the premises.

18 Claims, 7 Drawing Sheets

ILLEGAL DRUG DETECTOR AND METHOD OF ITS USE

FIELD OF THE INVENTION

The invention relates to an apparatus and/or method to detect and report the presence of illegal drugs to at least one interested party.

BACKGROUND OF THE INVENTION

The manufacture and/or use of illegal drugs are believed to pose a great threat to real property and personal welfare across the United States. Manufacturing methamphetamine alone can be extremely costly to property owners as well as dangerous to those who inhale fumes generated during the manufacturing process. The average clean up cost of a lab can easily run into thousands of dollars. Often this clean up cost is borne by insurance companies or land owners after rogue tenants perform unauthorized activities. The health risks to the occupants are more difficult to quantify.

One of the existing technologies that detect air contamination is called gas chromatography (GC). Currently, GC systems are bulky, expensive, and slow. High speed and affordable detection systems are believed to be needed for real time detection of illegal drugs such as meth labs. Current gas chromatography systems available are not believed to be practical for such use.

A second technology uses the concept of mass spectrometry. Beside their cumbersomeness, mass spectrometry systems are believed to be very expensive and not suitable for a real time detection system.

The inventor is not aware of the availability of any stand alone portable low cost system that is capable of detecting, in real time, multiple illegal drugs at the same time. The only known affordable and portable technology for detecting meth labs in the United States is done after a meth cook has already taken place using meth scanners.

This invention is motivated by the lack of available technology sophisticated enough to perform warning about the presence of illegal drugs in real time, yet simple, portable, and rugged enough to be easily deployed.

Currently no device is known to be available to automatedly detect the manufacturing and/or use of illegal drugs and warn interested parties of such activity. Accordingly, there is believed to be a need for sensors configured to detect and advise others of the presence of likely illegal drug activity and whereby an alarm is generated to provide notification to at least one interested party such as a property owner of likely illegal drug activity at a particular location.

SUMMARY OF THE INVENTION

It is an object of many embodiments of the present invention to provide a device with a sensor that senses fluid samples coupled to a processor that performs an analysis to determine whether or not there are pre-identified substances in the air sample at sufficient quantity to likely represent the presence of illegal drug activity at the premises. When the processor determines that at least one or more threshold levels of particular substances are present, then a notification is then provided to a communication system such as a loud alarm, wired and/or wireless communications to interested parties. Through such communication, an appropriate party and/or proper authority could be notified.

It is another object of many embodiments of the present invention to provide a sensor connected to a processor and a communication transmitter whereby upon taking a fluid and ascertaining the presence of at least one of a threshold substance, an alarm condition is established which is then communicated as a likely presence of an illegal drug to at least one interested party possibly including the appropriate authorities.

Another objective of many embodiments this invention is to warn, in real time, about the presence of a variety of air contaminations in closed space such as motels, hotels, dorms, etc. Of particular interest to many embodiments of this invention is the detection of meth labs and marijuana smoking. Some embodiments of the apparatus can also be used to detect cigarette smoking in areas where smoking is not allowed. To achieve such goal, an array of low cost sensors may be used by the apparatus for at least some embodiments. Furthermore, to achieve robust detection, the concept of sensor data fusion can be used to integrate information provided by an array of at least two sensors.

The proposed apparatus is preferably a relatively low cost, standalone, possibly portable, and may consist of a data acquisition subsystem to acquire the array of sensor data, a central processor that fuses the sensor data and decides if air contamination is present, then classifies the type of contamination for at least some embodiments. Once a detection is confirmed, a built in wireless communication subsystem sends a warning to alert appropriate authorities. The same or similar, or dissimilar, alert may be sent to a nearby server that displays the location, type and level of contamination of the contaminated area. The device may also be equipped with an intruder detection subsystem to keep unauthorized users away.

Accordingly, in accordance with a presently preferred embodiment of the present invention, a drug sensing system preferably includes a sensor coupled to a processor whereby the sensor obtains fluid samples such as air samples either continuously or at intervals, such as periodic. The air samples are then preferably analyzed to detect the presence of at least one, if not a plurality, of pre-identified substances. Upon detection of at least a threshold quantity of one or more substances, an alarm condition is identified. Substances tested for are not normally found in the locations where drug activity does not normally occur.

Upon the establishment of an alarm condition, at least a communication is made to at least interested party such as the authorities including law enforcement and/or other governmental agency or department, the land owner, or third parties in the surrounding area such as with an audible alarm or other device, possibly including wired or wireless communications such as the sending of an e-mail to the property owner, text messaging various parties, automated phone calls to various parties including alarm companies and/or other communication methods. A GPS unit could also be utilized to precisely identify the premises to at least some of the parties that could be notified.

While sophisticated smoke alarms provide similar notifications of the presence of a fire under some conditions to third parties through alarm companies, there is no known smoke detector or other detector which analyzes to distinguish between the smoke of non-illegal activity such as cigarette smoke and marijuana smoke or smoke associated with the manufacture of methamphetamine or other illegal drug. Accordingly, the applicant sensing and evaluation technology is believed to be quite different than prior art smoke detectors.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
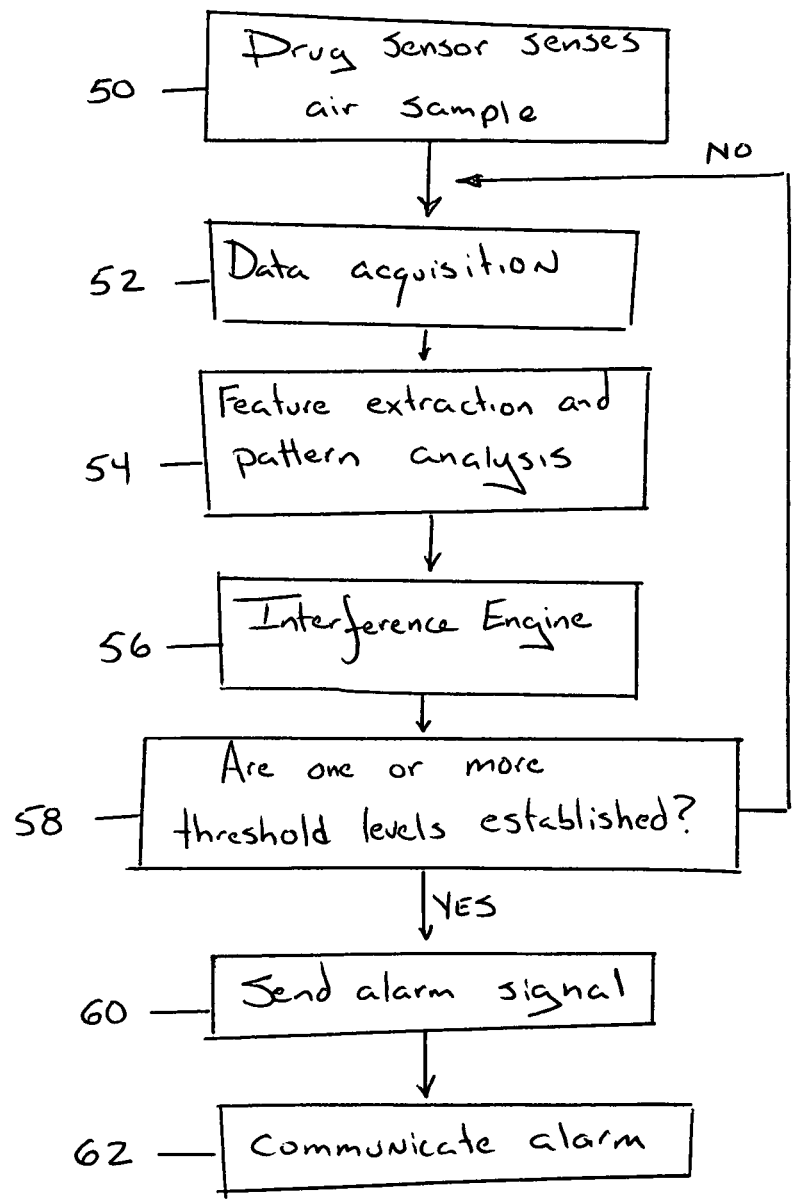
FIG. 1 is a flow chart showing the process of a presently preferred embodiment of the present invention.
Figure 2:
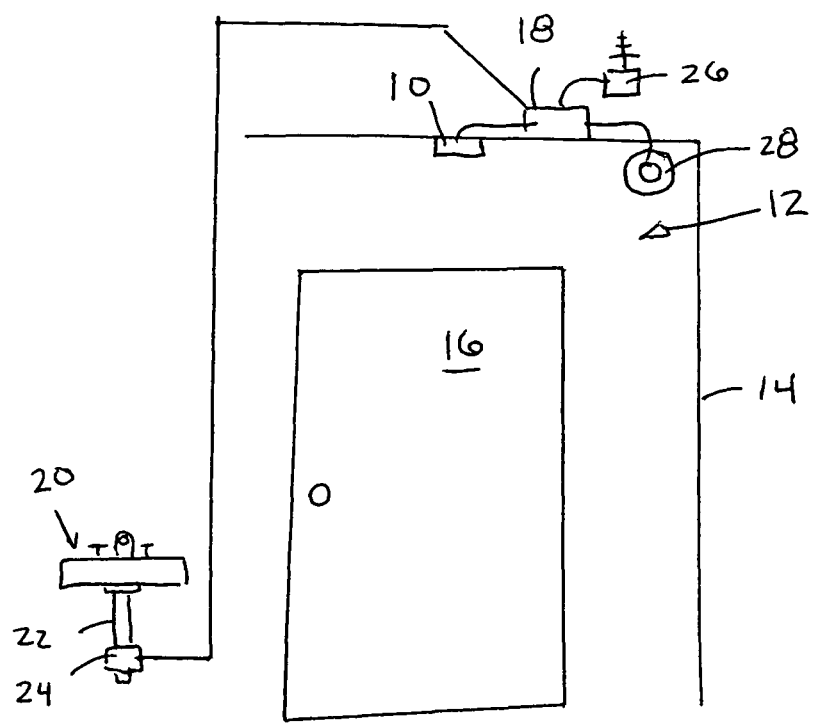
FIG. 2 is a plan view of a portion of a room having a sensor of the presently preferred embodiment in communication with an alarm system and a communication system performing the steps of shown in the flow chart of FIG. 1.

FIGS. 1 and 2 show a presently preferred embodiment in operation. Specifically, at least one sensor 10 is shown in FIG. 2 in a premises such as a hallway or other room 12 which could be a kitchen, a passageway in an apartment building or other appropriate location whether inside or outside of a building 14. Other structures such as storage buildings, vehicles and other places of concern could be an appropriate premises. The sensor(s) 10 could be sensing material either interior to the room 12 or external to the room 12 such as on the other side of the door 16 such as in an apartment building or the like.

As shown in FIG. 1 at step 50, a sensor 10 such as an air sensor or other fluid sensor obtains at least one sample. Multiple samples may be taken by multiple sensors 10 for some embodiments. The data acquisition step at step 52 is then employed whereby the fluid sample(s) is/are converted to data. Feature extraction such as through filtering and pattern analysis is then performed at step 54 to attempt to extract relevant data from non-relevant data. An interference engine 56 may then be employed such as by one or more processor(s) 18 or other devices which can also perform steps 54 and others. The processor(s) 18 can make the determination of step 58 as to whether or not one or more threshold amounts of a particular substance are located in the fluid sample at the premises.

Data may be extracted from the fluid sample such as by an infrared gas analysis or other appropriate technology, such as ionization, infrared imagery, or other suitable technology. The data would correspond to amounts of detected substances. This data is preferably digital in nature although analog or other systems could be employed for at least some embodiments.

Other recognition techniques and/or systems could assist in the evaluation process. A GPS unit 19 could provide physical inspection of the premises and/or detector 10 for at least some embodiments.

Due to the fact that there are currently no affordable sensors, and systems, that specialize in the measurement of either of marijuana smoke or meth lab vapors, the idea is to measure air contaminations that are generated as a result of using such drugs such smoking marijuana and cooking meth. Therefore, instead of using a single sensor, an array of sensors will be deployed at the same time for the detection of a particular illegal drug. The number of sensors may depend on the number of known independent components in each drug that can be measured preferably using available low cost sensors. The proposed design is flexible and can easily accommodate an arbitrary number of current and future sensors. This is explained in some details next.

Methamphetamine usage and production is growing to alarming levels throughout much of the United States. These labs destroy buildings in which they take place and are very expensive to clean up. Early detection of these labs is crucial. A wide variety of chemicals are found in meth labs. They include Acetone, Methanol, Ammonia, Benzene, Ether, Freon, Hydriodic Acid, Hydrochloric Acid (HCL Gas), Iodine Crystals, Lithium Metal, Sulfuric Acid, etc.

Similarly, Marijuana smoking air contaminants include Hydrogen cyanide, Carbon Dioxide, Ammonia, Cyanogen, Isoprene, Acetaldehyde, and Acetone. Some of these contaminants also appear in cigarette smoking.

By one or more substance, a particular set of components can be expected in the smoke of marijuana such as THC and possibly other components such as hydrogen dyanide, carbon dioxide, ammonia, cyanogen, isoprene, acetaldehyde and acetone, cannabinoids at least some of which would not otherwise be present in the burning of such articles as wood or cigarettes.

For example, when the precursor drug of methamphetamine is extracted, it is possible that byproducts such as vapors of ephredrine or pseudoephredrine as well as binder from tablets, coffee filters or other materials could be detected by the inner sampler. Vapors of ephredrine are not normally present at most premises.

Depending on whether the red phosphorous method or the anhydrous ammonia method is utilized, different byproducts can also be detected by the sensor 10. Specifically, with the red phosphorous method, it is possible that byproducts including iodine, red, white or yellow phosphorous, sodium hydroxide, phosphine gas, hydrogen chloride gas, coffee filters, solvent or other byproducts could possibly be detected.

In the anhydrous ammonia method, byproducts such as coffee filters, excess metal, hydrogen chloride gas could provide somewhat dangerous byproducts. Of course, the different components themselves such as Hydroiodic acid (HI), hydrochloric (muriatic) acid, sulfuric acid, sodium hydroxide (lye), sodium chloride, salt, isopropyl alcohol, ethyl alcohol, methyl alcohol, hydrogen peroxide, naphtha, charcoal lighter fluid, acetone benzene, toluene, ethyl ether, Freon, hydrogen chloride gas, or chloroform, ascetic acid, methyl-ethyl-ketone (MEK), or hydrophosphoric acid could be identified as components. Particularly if multiple concentrations of unexpected concentrations in any of these components are detected, it is likely that the processor 18 could then identify the possible presence of the manufacture of methamphetamine.

In the anhydrous ammonia method, various components such as sodium, potassium, or lithium metal could be identified as well as anhydrous ammonia, ether or other solvent such as isopropyl alcohol, ethyl alcohol (ethanol), iodine crystals, methyl alcohol (methanol), hydrogen chloride gas, hydrochloric (muriatic) acid, sulfuric acid, sodium chloride (salt), toluene, naphtha (Coleman fuel), Freon, ethyl ether (starter fluid), chloroform, and methyl-ethyl-ketone (MEK) could be identified by the sensor(s) 10.

After the precursor drug formation (salting out) process could be identified by the components used, namely, rock salt or table salt together with sulfuric or muriatic acid and filters. Of course, byproducts including excess salt, sulfuric or muriatic acid, hydrochloric acid, hydrogen chloride gas, coffee filters, meth, solvent from above phases, possibly acetone could also be produced. At least one of the products or byproducts could be detected by the sensor 10.

Regardless of how the components are made, hydrogen cyanide could be expelled, formaldehyde, hydrogen chloride, hydrochloric acid, methylamine, phosphine, ammonia, hydrogen and other gasses or compounds could be produced and possibly identified by the applicant's methodology and device.

In addition to taking air samples, it may also be possible to process liquid samples such as could be tested when processing the sinks drains through the sewage system. In this case, instead of taking air samples, liquid contaminants could possibly include toluene, pyridine, petroleum ether, methylene chloride, methanol, isopropanol, hexane, ethyl ether, dioxane and any number of other hazardous materials produced by the methamphetamine production method.

FIG. 2 shows a sink 20 with a drain 22 to which a liquid sensor 24 is connected which could be utilized to detect liquid contaminants associated with the manufacture of methamphetamine or other drug activity.

Of course, it is likely that the sensors 10, 24 will not be disclosed to the occupants of the premises such as by being installed by the landlord and configured to automatically operate with the operation of the electrical or other sources of the building 14 or other premises.

Once one or more processors 18 detect one or more threshold levels such as by requiring the presence of hydrogen chloride and hydrogen cyanide together in at least minimal detectable amounts. A minimal threshold may be discovered or established at step 58 and an alarm signal can be sent in step 60 such as to a communications device 26, an audible alarm 28 or other device. At that point, an alarm 62 is communicated such as by the communications device 26 either wirelessly or otherwise such as by calling, texting, e-mailing or otherwise alerting an interested party such as the police, sheriff's office, appropriate government agency or agencies, the property owner, a landlord, a property management company, or various combinations of these and/or other parties. This way, the automated detection of the illegal production of at least certain illegal drug activity can be detected and identified so that a drug problem can potentially be stopped at least at that location.

Furthermore, such activities as the casual smoking of marijuana can also be identified as components of smoke of marijuana would include delta-9-tetrahydrocanniball (THC) and other cannabinoids such as cannabindiol (CBD), cannabanol (CBN) and tetrahydrocannabrivian (THCB).

Of course, there is no nicotine in marijuana and the sensor in the presence of nicotine could create a situation in the processor 18 to possibly negate a finding of potential marijuana smoke which might otherwise be triggered. Finding a certain amount of nicotine in the sample may also raise the level of a component such as THC required to reach the threshold.

While the use of marijuana is discussed as being an illegal activity which can be monitored with the method and system described herein, as well as the production of methamphetamine, other illegal activity could be monitored and reported with appropriate sensors 12,24 processors 18 and communication systems 28,26 as would be known by those of ordinary skill in the art. The smoking of cocaine could be monitored for various chemical byproducts. The purification or manufacture of other illegal substances could also be monitored based on components and/or byproducts used or generated during these processes.

One proposed embodiment would include the provision of commercially available low cost sensors that exhibit high sensitivity to air contamination whenever one or more of the chemicals used in illegal drugs, such as meth cook or marijuana smoking, are present. As an illustration, Table 1 shows available low cost commercial Figaro sensors and their industrial applications.

TABLE 1

| Commercially Available Low Cost Sensors | | | |
| --- | --- | --- | --- |
| TGS 2600 | TGS 2602 | TGS 2620 | TGS 2610 |
| Air cleaners | Air cleaners | Alcohol testers | Residential LP leak |
| Ventilation control | Ventilation control | Organic vapor detectors | Portable LP detectors |
| Air quality monitors | Air quality monitors | Solvent detectors | LP gas and vapor detection |
| | VOC monitors | | |
| | Odor monitors | | |

Research was conducted to evaluate the sensitivity of air contamination due to the presence of some of the chemicals discussed previously. This is summarized in Table 2.

TABLE 2

| Sensitivity Matrix | | | | |
| --- | --- | --- | --- | --- |
| Chemical | TGS 2600 | TGS 2602 | TGS 2620 | TGS 2610 |
| Cannabinoids | No/very low | low | high | high |
| Nicotine | No/very low | low | high | high |
| Ammonia | Low | high | low | low |
| Ether | Low | low | high | high |
| Toluene | Low | low | Medium | Medium |
| Turpentine | Low | low | high | high |
| Methanol | Medium | Medium | high | Medium |
| Freon | Low | Low | high | high |
| Phosophine Gas | Medium | Medium | low | low |
| Isoprene | Low | Low | high | high |
| Hydrogen | High | Medium | low | low |
| Ethanol | Low | Low | high | Medium |

A closer look at this table shows that a single sensor may be sensitive to more than on chemical. The sensitivity also varies whenever a mixture of these chemicals takes place. This poses a challenging problem as far as detecting the presence of illegal drugs with an acceptable level of confidence.

To overcome some of these difficulties, an array of sensors may be used in many embodiments. Advanced signal processing techniques including adaptive filtering, principal component analysis (PCA) can be used to preprocess sensor data. The preprocessed data of all the sensors can then be fused together to generate data that would have been produced by a "super sensor" capable of directly measuring the different contaminations present in the air.

Figure 3:
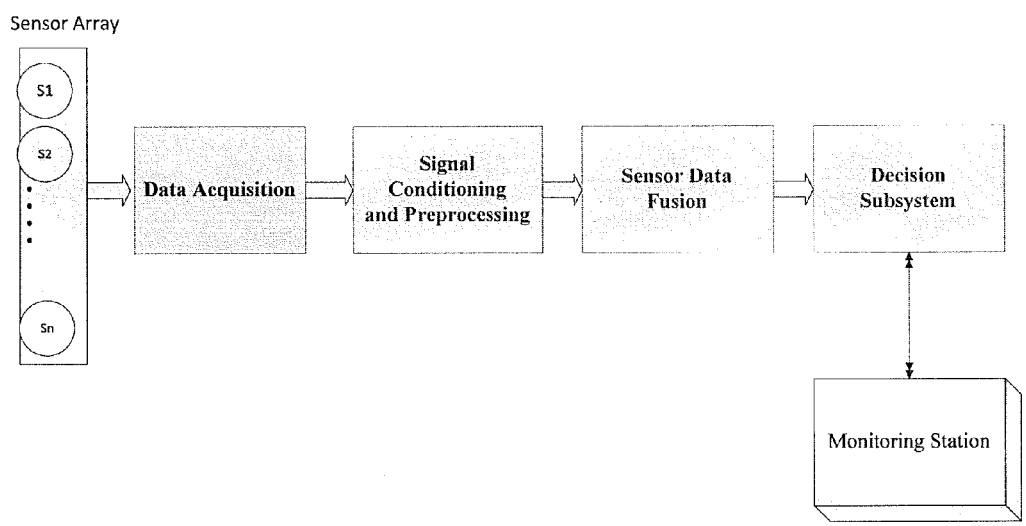
FIG. 3 is a diagrammic representation of the presently preferred embodiment of the invention.

Data fusion can be analogous to the ongoing cognitive process used by humans, FIG. 3, to continually integrate data from their sensors to make inferences about the external world. Equipped with five types of sensors: vision (eyes), hearing (ears), taste (tongue), smell (nose), and touch (fingers), humans make complex decisions all the time, even when the information provided by individual sensor is fuzzy or incomplete, of their environment all the time (FIG. 3). Data fusion could, if done properly, provide a better foundation for decision making than what could be achieved from relying on a single source of information.

Figure 4:
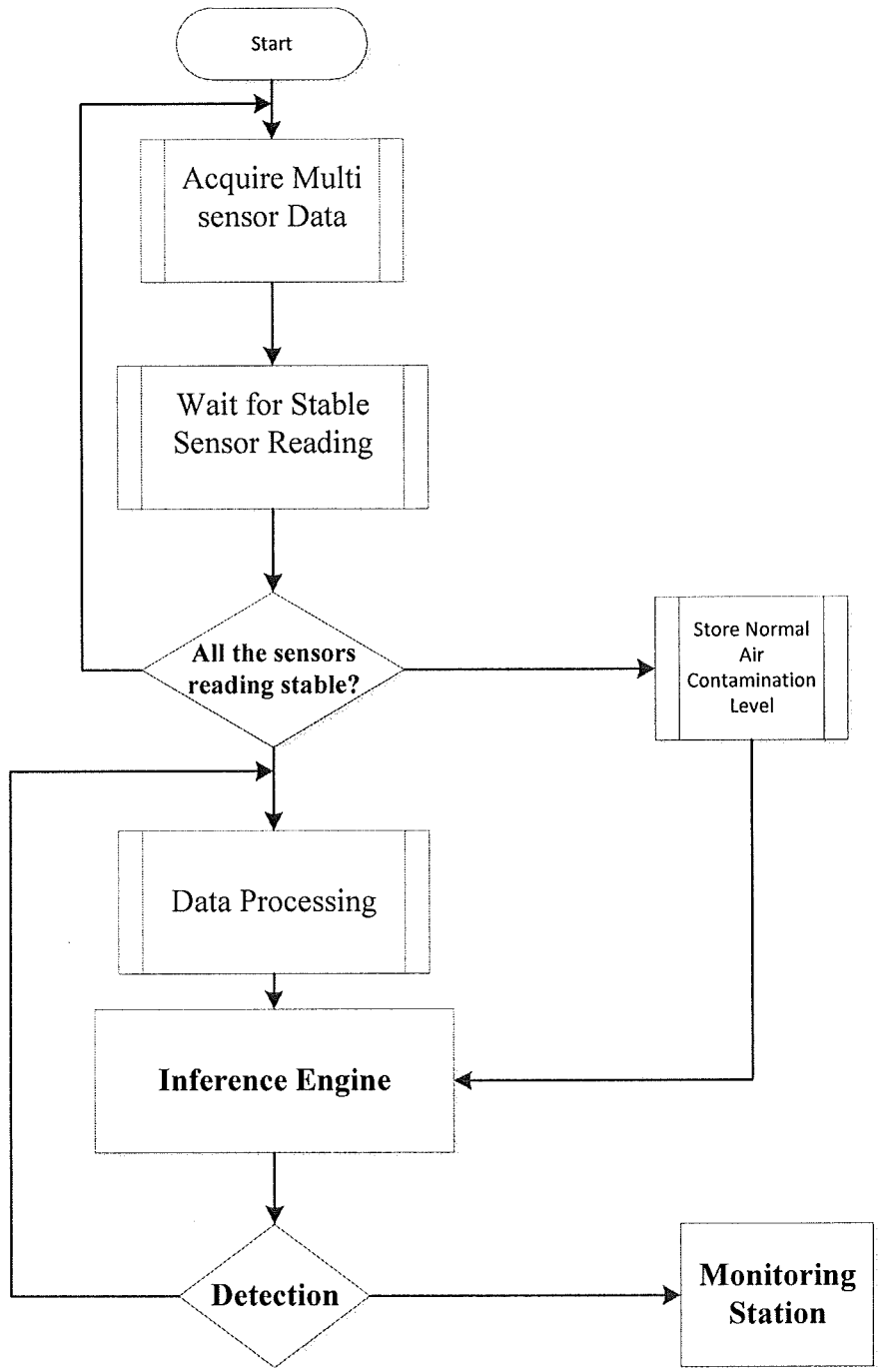
FIG. 4 is a flow chart showing an alternative embodiment of the presently preferred embodiment of the present invention.
Figure 5:
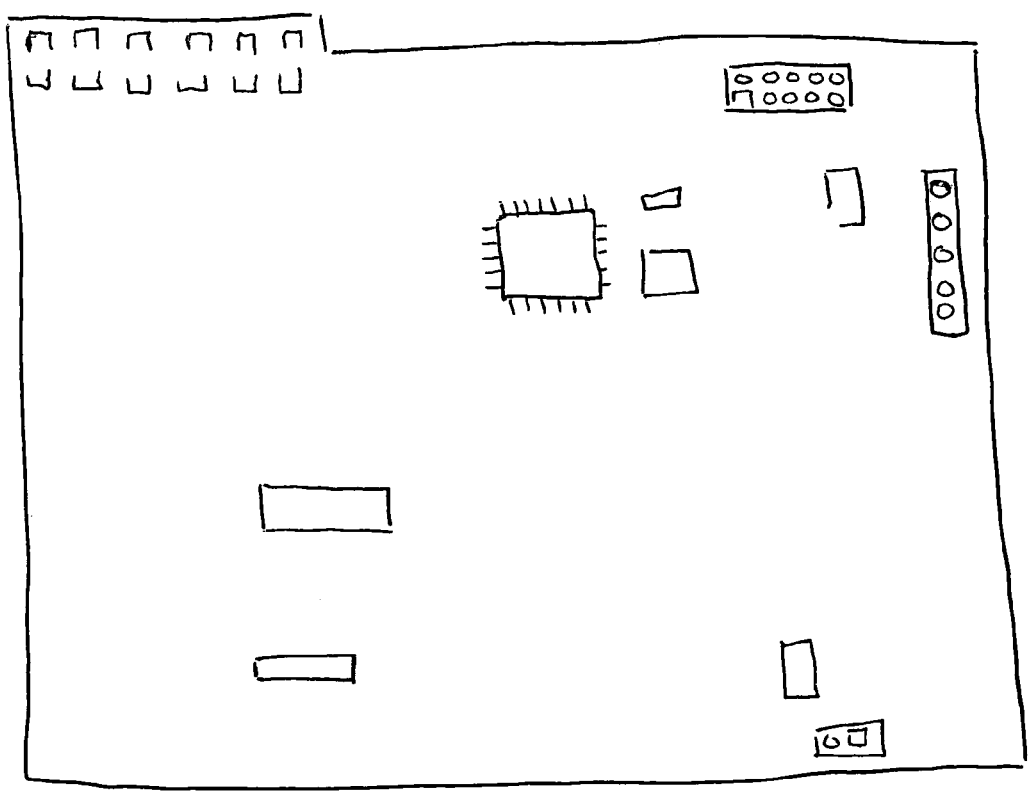
FIG. 5 is a circuit diagram of a processor utilized in the presently preferred embodiment of the present invention.

In this application, human biological sensors are replaced with relevant commercially available low cost sensors and the brain is replaced with a decision system. The conceptual design of the system is summarized in FIG. 3, while the real time detection flowchart is shown in FIG. 4. S1, S2 and Sn are sensors 10 of various capabilities.

Figure 6:
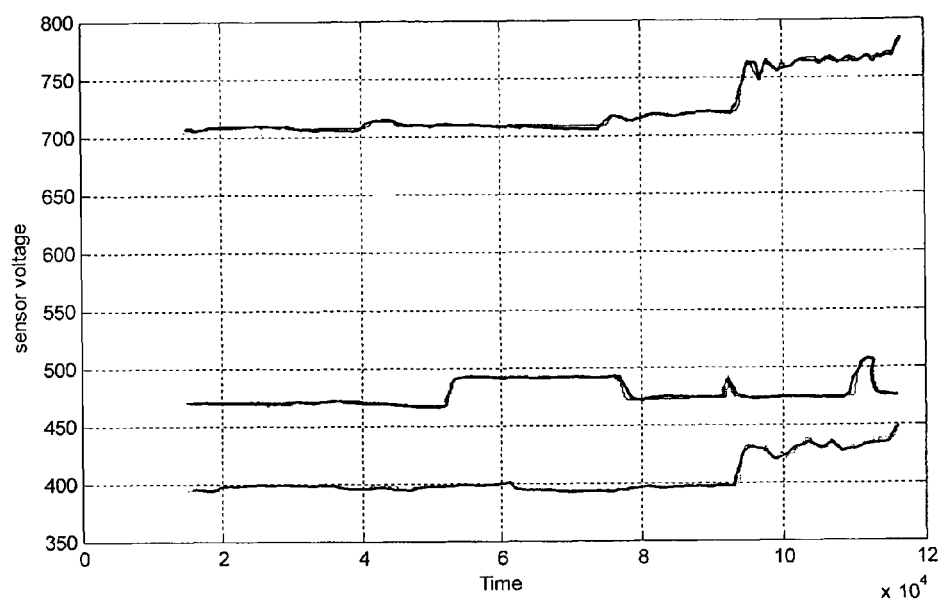
FIG. 6 is a graph of voltage versus time for a first field test of the presently preferred embodiment of the present invention.
Figure 7:
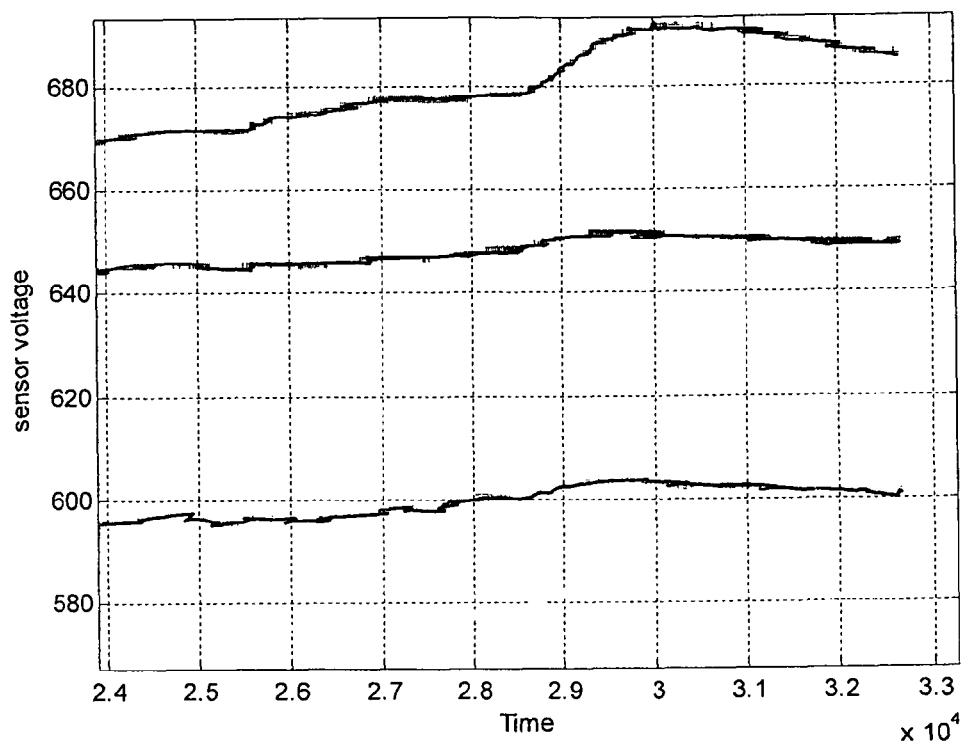
FIG. 7 is a graph showing the voltage versus time for a second field test of the presently preferred embodiment of the present invention.

The apparatus was tested in a closed space under no contamination and marijuana smoking environment. FIGS. 6 and 7 show the device response to burning marijuana. As can be seen from these figures, the two sensors dedicated to the presence of marijuana smoking show higher sensitivity than the ones used to detect the presence of meth lab cooks but other embodiments may produce different results.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. An automated illegal drug detector comprising:
   at least two sensors configured to each receive a fluid sample from a location at a premises and provide data relative to the sample;
   a processor configured to receive data from the at least two sensors, and compare information in the data to at least one threshold to ascertain whether there is at least one substance corresponding to at least one of a chemical used in and a byproduct of a substance associated with an illegal activity selected from the group of illegal drug use and illegal drug manufacture which would not normally be expected absent the illegal activity; and
   wherein the processor provides higher sensitivity than obtainable from either of the at least two sensors;
   if the at least one threshold is reached, generating an alarm signal, and communicating an alarm at least one of locally and remotely.

2. The automated illegal drug detector of claim 1 wherein the alarm signal is sent to one of an audible alarm locally and a communication system which sends a message to an interested party remotely.

3. The automated illegal drug detector of claim 2 wherein the communications system communicates by at least one of a text message, an e-mail message and an automated phone call.

4. The automated illegal drug detector of claim 1 further comprising a GPS unit, and the alarm signal contains GPS coordinates of the illegal activity.

5. The automated illegal drug detector of claim 4 wherein at least two sensors are selected from the group of TGS 2000, TGS 2602, TGS 2620, and TGS 2610.

6. The automated illegal drug detector of claim 1 wherein upon indication of at least some substance not indicative of illegal activity, raising the at least one threshold.

7. The automated illegal drug detector of claim 1 wherein the fluid sample is an air sample.

8. The automated illegal drug detector of claim 1 wherein one of the at least two sensors is gas analysis based.

9. The automated illegal drug detector of claim 1 wherein one of the at least two sensors is infrared based.

10. The automated illegal drug detector of claim 9 wherein one of the at least two sensors relies on one of infrared gas analysis and infrared imaging.

11. The automated illegal drug detector of claim 9 wherein one of the at least two sensors relies upon ionization of the fluid sample.

12. The automated illegal drug detector of claim 1 wherein the alarm signal is sent to law enforcement officials remotely from the premises.

13. The automated illegal drug detector of claim 12 wherein the processor performs pattern recognition techniques to determine if at least one threshold is reached.

14. The automated illegal drug detector of claim 1 wherein the data provided to the processor is digital data.

15. The automated illegal drug detector of claim 1 wherein the alarm is generated both locally at the premises and remotely.

16. The automated illegal drug detector of claim 6 wherein the processor integrates data from the sensors relative to the at least one threshold.

17. The automated illegal drug detector of claim 1 wherein the fluid sample is a sink or bathroom water sample.

18. An automated illegal drug detector comprising:
   an automated illegal drug detector comprising:
   at least two sensors configured to each receive a fluid sample from a location at a premises and provide data relative to the sample, wherein at least two sensors are selected from the group of TGS 2000, TGS 2602, TGS 2620, and TGS 2610;
   a processor configured to receive data from the at least two sensors, and compare information in the data to at least one threshold to ascertain whether there is at least one substance corresponding to at least one of a chemical used in and a byproduct of a substance associated with an illegal activity selected from the group of illegal drug use and illegal drug manufacture which would not normally be expected absent the illegal activity; and
   a GPS unit, and the alarm signal contains GPS coordinates of the illegal activity;
   wherein the processor provides higher sensitivity than obtainable from either of the at least two sensors; and
   if the at least one threshold is reached, generating an alarm signal, and communicating an alarm at least one of locally and remotely.

* * * * *